US00PP13858P29

(12) United States Plant Patent
Jaques

(10) Patent No.: US PP13,858 P2
(45) Date of Patent: Jun. 3, 2003

(54) PLECTRANTHUS PLANT NAMED 'PLEPALILA'

(76) Inventor: Roger Francois Jaques, Kirstenbosch Botanical Institute, Private Bag X7, Claremont 7735 (ZA)

( * ) Notice: Subject to any disclaimer, the term of this patent is extended or adjusted under 35 U.S.C. 154(b) by 0 days.

(21) Appl. No.: 10/034,484

(22) Filed: Dec. 28, 2001

(51) Int. Cl.[7] ..... A01H 5/00
(52) U.S. Cl. ..... Plt./263; Plt./373
(58) Field of Search ..... Plt./263, 373

(56) References Cited

PUBLICATIONS

UPOV ROM GTITM Computer Database, GTI JOUVE Retrieval Software 2002/05, citation(s) for 'Plepalila'.*
wysiwyg://7/http://forums.gardenweb.com/forums/load/annuals/mg/0923351830715.html Plant to recommend:mona lavender plectranthus.*

Tom MacCubbin II, Plant Profile: Mona Lavender Plectranths Orlando Sentinel, Nov. 30, 2002.*

Connie Krochmal, Sensational Container Plants for Fall http://www.smallgarden.info/sensational_container_plants_for.htm.*

Andrew Hankey, Plectranthus, Witwatersand National Botanical Garden, South Africa, Apr. 2001.*

* cited by examiner

*Primary Examiner*—Bruce R. Campell
*Assistant Examiner*—W C Haas
(74) *Attorney, Agent, or Firm*—Wood, Phillips, Katz, Clark & Mortimer

(57) ABSTRACT

A new and distinct Plectranthus plant named 'Plepalila' is shown herein and described.

2 Drawing Sheets

LATIN NAME OF THE GENUS AND SPECIES OF PLANT CLAIMED

*Plectranthus hybrida.*

VARIETY DENOMINATION

Figure 1:
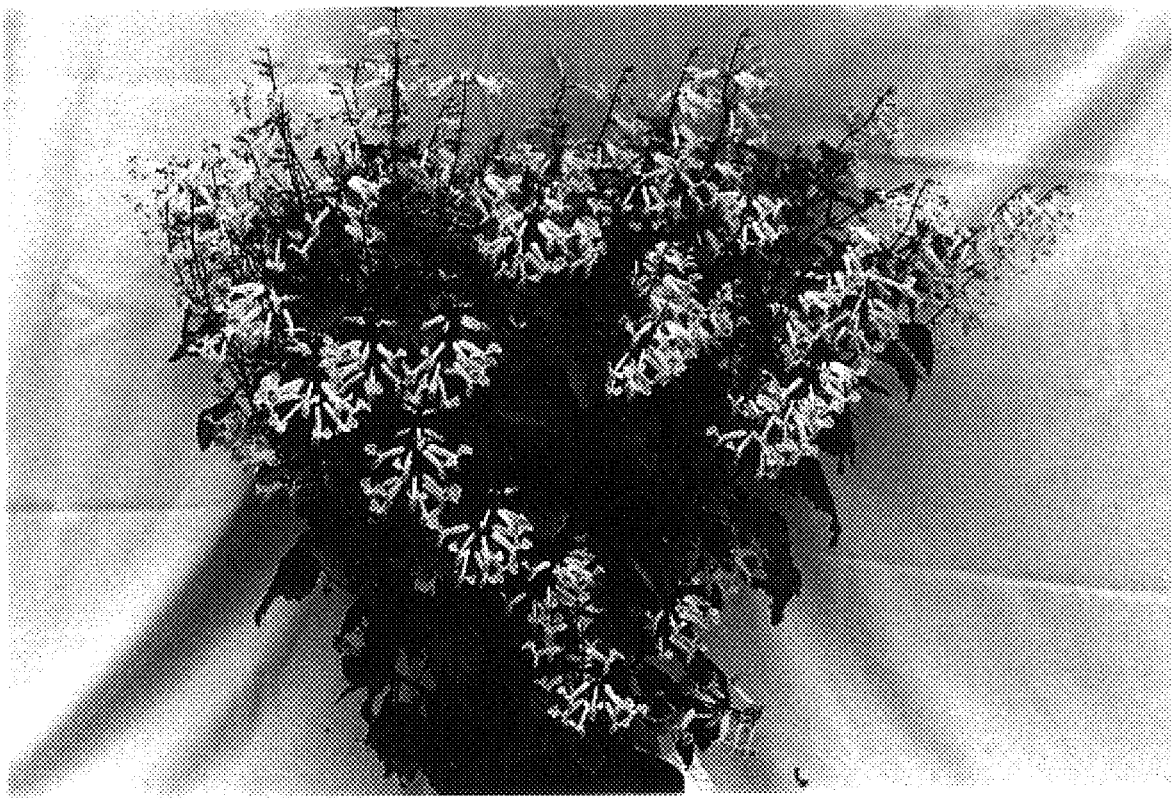
Figure 2:
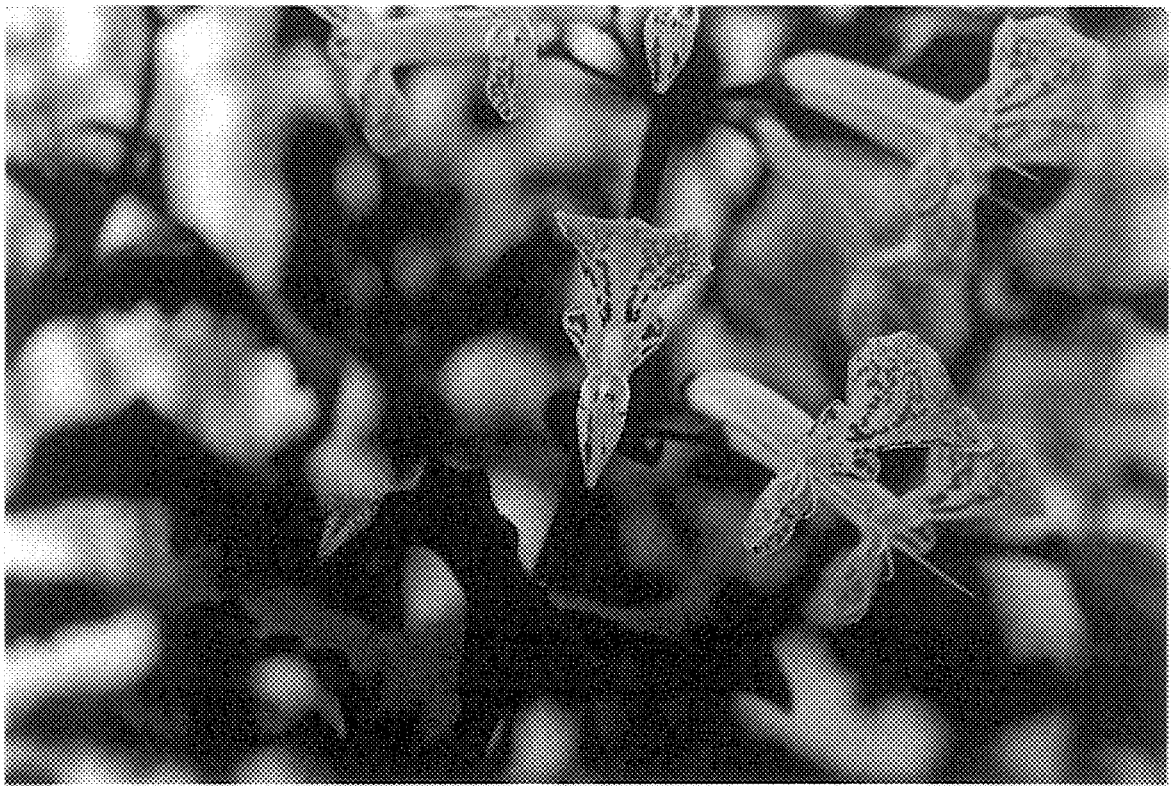

Plepalila.

BACKGROUND OF INVENTION

The present invention comprises a new and distinct Plectranthus plant, hereinafter referred to by the cultivar name 'Plepalila'. More specifically, the breeding program which resulted in the production of the new cultivar was carried out in Cape Town, Western Cape, South Africa. The female or seed parent of 'Plepalila' was a proprietary *Plectranthus saccatus* designated 800/77 (unpatented). The male or pollen parent of 'Plepalila' was a proprietary *Plectranthus hilliardiae* designated 146/92 (unpatented). The resulting seed was collected and germinated. From the progeny, a single plant was selected in 1998.

Asexual reproduction of the new cultivar by terminal or stem cuttings taken during 1999 at Claremont, South Africa and during 2000–2001 at West Chicago Ill., USA has demonstrated that the characteristics of the new cultivar as herein described are firmly fixed and are retained through successive generations of such asexual propagation.

SUMMARY OF THE INVENTION

It was found that the cultivar of the present invention:
(a) Exhibits an upright bushy habit,
(b) Forms lavender flowers, (c) Forms dark green foliage with dark purple underside and
(d) Exhibits a vigorous growth habit.

'Plepalila' has not been observed under all possible environmental conditions to date. Accordingly, it is possible that the phenotype may vary somewhat with variations in the environment, such as temperature, light intensity, and day length.

When the new cultivar of the present invention is compared to its male parent (non-patented) it exhibits shorter petioles, of a different color and leaves of a different texture and color as detailed in Table A.

BRIEF DESCRIPTION OF PHOTOGRAPHS

The accompanying photographs show as nearly true as it is reasonably possible to make the same in color illustrations of this type, typical flower and foliage characteristics of the new cultivar. The plants were grown in a greenhouse at West Chicago, Ill., USA.

Photo A illustrates the general growth habit of 'Plepalila'.

Photo B illustrates individual flowers of 'Plepalila'.

DETAILED BOTANICAL DESCRIPTION

The chart used in the identification of colors described herein is The R.H.S Colour Chart of The Royal Horticultural Society, London, England. The color values were determined on Jul. 27, 2001 in West Chicago, Ill. The readings were taken between 10:00 and 11:45 p.m. under natural light conditions. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night. Plants used for the following descriptions and measurements were grown for fourteen (14) weeks from rooted cuttings in a greenhouse in West Chicago Ill.

Botanical classification: *Plectranthus hybrida* cultivar Plepalila.

Propagation:

*Type cutting.*—Terminal tip.

*Time to form roots.*—Approximately 21–28 days.

Plant description:

*Crop time.*—Eight to eleven weeks in a 20 cm pot.

*General appearance and form.*—Upright bushy shrub.

*Plant height.*—Approximately 44.3 cm.

*Plant spread.*—Approximately 36.4 cm.

*Number of branches.*—Average of 4 with approximately 12 leaves per branch.

*Branch.*—Shape: Square. Diameter: Approximately 1 cm at base. Color: 137A with streaks of 79A. Texture: Sparsely pubescent, gland-dotted. Some long hairs at nodes.

*Internode length.*—At third node from tip: Approximately 4.8 cm.

Foliage description:

*Form.*—Single.

*Shape.*—Ovate.

*Margin.*—Crenate-serrate, undulate.

*Apex.*—Sharply acute.

*Base.*—Cuneate.

*Arrangement.*—Opposite.

*Venation pattern.*—Pinnate(reticulate).

*Surface.*—Appearance: Dull, velvety. Texture: Upper and lower surfaces: Papillose-hispid.

*Color of mature foliage.*—Upper surface: Darker and more yellow than 139A with veins of 139A.

*Color of mature foliage.*—Lower surface: Slightly lighter than 79A with veins of 79A.

*Size.*—Approximately 7.7 cm in length. Approximately 5.6 cm in width.

*Petiole.*—Shape: square. Length: Approximately 5.1 cm. Diameter: Approximately 2.3 mm. Color: Upper surface is 139A, side and lower surfaces are 79A.

Flower description:

*Outdoor flowering habit.*—'Plepalila' flowers naturally under short days, in late summer through early fall.

*Inflorescence type.*—Raceme, arising from upper most pair of leaves.

*Flower arrangement.*—Solitary, shortly pedicelled in 3 flowered verticils positioned at right angles to the stem.

*Flower type.*—Bilabiate. Upper lip is 4 lobed—2 central lobes 1.2 cm long and 5 mm wide and 2 lateral lobes 5 mm long and 1 mm wide. Lower lip is 2 lobed, concave, boat-shaped, 7 mm long and 4 mm wide.

*Pedicel.*—Length: Approximately 6 mm. Diameter: Approximately 1 mm. Texture: Finely glandular-hispid. Color: 79A.

*Fragrance.*—Slightly herbal.

*Bud.*—Length: 1.7 cm. Width: 3 mm.

*Flower.*—Length: Approximately 2.5 cm. Width: Approximately 5 mm. Appearance: Iridescent.

*Corolla tube.*—Flattened and bilaterally symetrical with slightly swollen base. Length: 1.7 cm. Width at base: Approximately 4 mm. Width at throat: Approximately 3 mm. Color: Between 85B and 85C.

*Limb.*—Color: Lips have background color of between 85B and 85C with small spots of between 89B and 89C which somewhat coalesce into splotches.

*Throat.*—Color: Between 85B and 85C.

*Calyx.*—Shape: Tubular. Two lipped with broad upper lip and lower lip comprised of four pointed lobes fused at base. Lateral pair are shorter than the central pair. Surface: Setulose. Length: Approximately 4 cm at flowering stage. Diameter: Approximately 2 mm. Color: Closest to 145C with ribs and tips of 79A.

*Reproductive organs.*—Androecium — Stamens: 4. One pair approximately 1 cm in length with 8 mm free, rest fused to corolla tube and a second pair approximately 8 mm in length with 6 mm free and rest fused to corolla tube. Anthers; two parted, oval, approximately 1.5 mm in length, between 95C and 95D in color. Gynoecium—One pistil, approximately 2.9 cm long. Stigma is two parted approximately 1 mm in length, between 95B and 95C in color. Style is approximately 2.7 cm in length, 95C in color. Ovary is approximately 1 mm in length, 144A in color. Pollen has not been observed.

Seed production: Seed production has not been observed.

Disease resistance: Resistance to diseases common to Plectranthus has not been observed.

TABLE 1

| | PLEPELILA | MALE PARENT |
|---|---|---|
| LEAF APEX | Sharply acute | Rounded |
| COLOR OF UPPER SURFACE OF LEAF | More yellow than 139A | 139A |
| COLOR OF LOWER SURFACE OF LEAF | 79A | 146B with very narrow band around margin of 79A. |
| APPEARANCE OF UPPER SURFACE OF LEAF | Dull, velvety | Shiny, waxy |
| PETIOLE COLOR | Upper surface: 137A Sides and lower surface: 79A | All sides: 146B |
| PETIOLE LENGTH | 5.1 cm | 2.5 cm |

I claim:

1. A new and distinct cultivar of Plectranthus plant named 'Plepalila' substantially as herein shown and described, which:

(a) Exhibits an upright bushy habit;

(b) Forms lavender flowers;

(c) Forms dark green foliage with dark purple under surface; and (d) Exhibits a vigorous growth habit.

* * * * *